US 6,695,835 B2

(12) United States Patent
Furuno et al.

(10) Patent No.: US 6,695,835 B2
(45) Date of Patent: Feb. 24, 2004

(54) LASER TREATMENT APPARATUS

(75) Inventors: Takahiro Furuno, Gamagori (JP); Mitsuo Yamamoto, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/079,697

(22) Filed: Feb. 22, 2002

(65) Prior Publication Data

US 2002/0120256 A1 Aug. 29, 2002

(30) Foreign Application Priority Data

Feb. 28, 2001 (JP) ........................................ 2001-053294

(51) Int. Cl.⁷ ............................................... A61B 18/20
(52) U.S. Cl. ................................ 606/9; 606/10; 607/89
(58) Field of Search ....................... 606/9–12; 607/88, 607/89

(56) References Cited

U.S. PATENT DOCUMENTS

| | | |
|---|---|---|
| 5,336,217 A | 8/1994 | Buys et al. |
| 5,743,902 A | 4/1998 | Trost |
| 6,077,294 A * | 6/2000 | Cho et al. ........................ 606/9 |
| 6,511,475 B1 * | 1/2003 | Altshuler et al. ............... 606/9 |
| 2001/0007068 A1 | 7/2001 | Ota et al. |

FOREIGN PATENT DOCUMENTS

| EP | 0172490 A1 * | 2/1986 | ........... A61B/17/36 |
|---|---|---|---|
| EP | 1 057 454 A2 | 12/2000 | |

OTHER PUBLICATIONS

U.S. patent application Ser. No. 09/692,319, Mukai, filed Oct. 20, 2000.

* cited by examiner

Primary Examiner—Roy D. Gibson
Assistant Examiner—Henry M. Johnson
(74) Attorney, Agent, or Firm—Oliff & Berridge, PLC (57) ABSTRACT

A laser treatment apparatus for performing treatment on a treatment part of a skin by irradiating the part with a laser beam for treatment is disclosed. The apparatus includes a laser output device which outputs the treatment beam; a hand-piece provided with at least a part of an irradiation optical system for irradiating the treatment beam of a predetermined spot size, the hand-piece being held in contact with the skin; a detector which detects a moved position of the hand-piece on the skin; and a controller which controls an ON/OFF state of laser irradiation based on the moved position detected by the detector and information on the spot size.

7 Claims, 6 Drawing Sheets

LASER TREATMENT APPARATUS

BACKGROUND OF THE INVENTION

1. Field of the Invention

The present invention relates to a laser treatment apparatus for performing treatment on a part to be treated (an affected part) of a skin by irradiating the part with a laser beam for treatment.

2. Description of Related Art

There has been known a laser treatment apparatus which irradiates a laser beam for treatment to a skin of a patient in order to perform depilation, removal of wrinkles, removal of birthmarks or other types of treatments. This type of treatment apparatus is usually provided with a hand-piece. At an aiming (alignment) work for laser irradiation, an operator moves the hand-piece to adjust an irradiation position (a spot position) of a laser beam to an intended position on a part to be treated, and performs the laser irradiation.

When the treatment part has a wide area, however, the operator has to move the irradiation position a number of times to completely perform laser irradiation to the entire treatment part. This would be a troublesome work for the operator.

SUMMARY OF THE INVENTION

The present invention has been made in view of the above circumstances and has an object to overcome the above problems and to provide a laser treatment apparatus capable of efficiently and appropriately performing laser irradiation to a treatment part having a wide area.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatment on a treatment part of a skin by irradiating the part with a laser beam for treatment, the apparatus including: laser output means which outputs the treatment beam; a hand-piece provided with at least a part of an irradiation optical system for irradiating the treatment beam of a predetermined spot size, the hand-piece being held in contact with the skin; detection means which detects a moved position of the hand-piece on the skin; and control means which controls an ON/OFF state of laser irradiation based on the moved position detected by the detection means and information on the spot size.

According to another aspect of the present invention, there is provided a laser treatment apparatus for performing treatment on a treatment part of a skin by irradiating the part with a laser beam or treatment, the apparatus including: a treatment laser beam output device; a hand-piece provided with a main part having at least a part of an irradiation optical system for irradiating the treatment beam of a predetermined spot size and a support part which is held in contact with the skin for supporting the main part above the skin; a rolling member provided in a side of the support part which is brought into contact with the skin; a rotation sensor for sensing a direction and amount of rotation of the rolling member; and a controller which detects a direction and amount of movement of the hand-piece on the skin based on the rotation direction and the rotation amount detected by the rotation sensor, and controls an ON/OFF state of laser irradiation based on the detected moved-position and information on the spot size

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
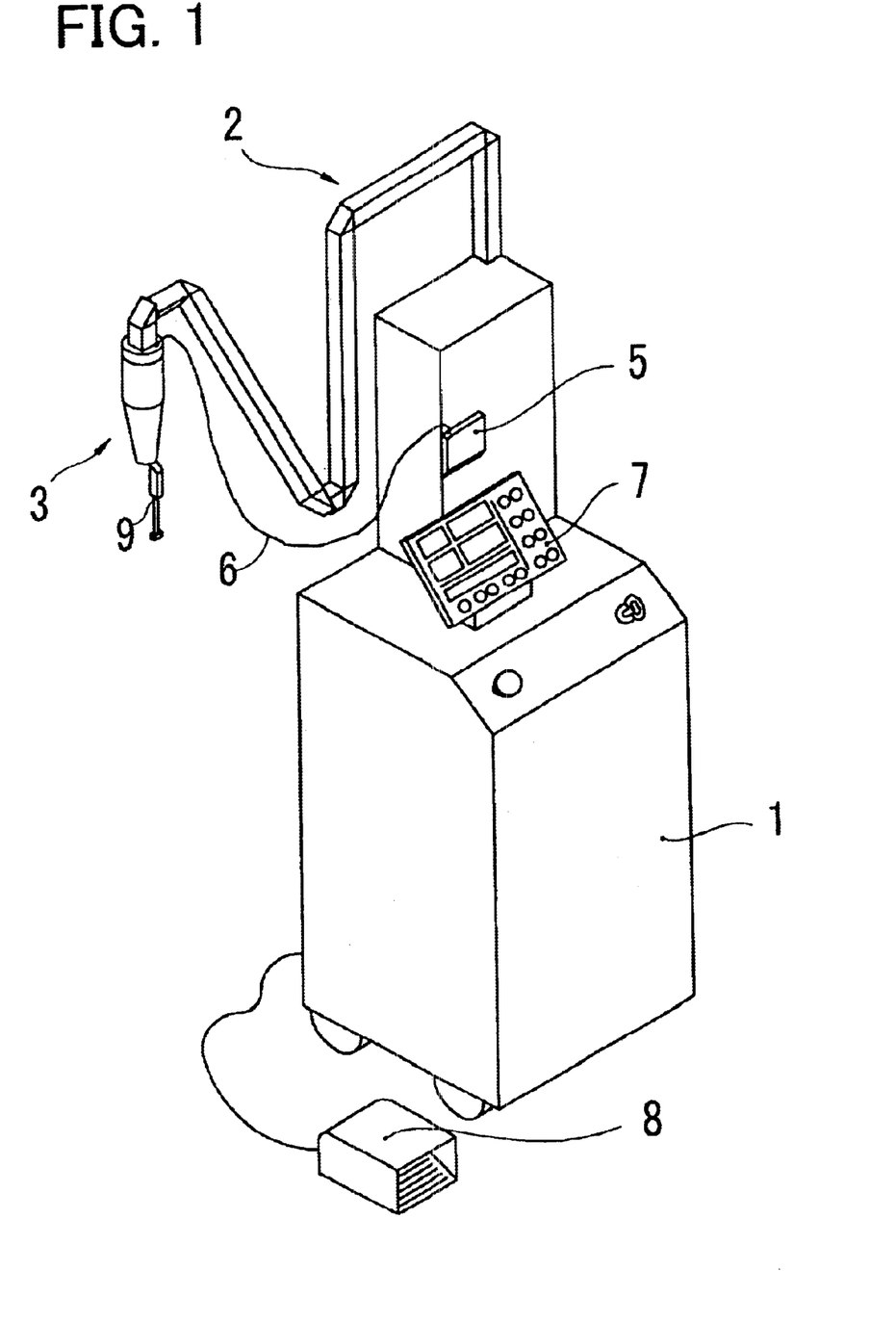
FIG. 1 is a schematic perspective view of a laser treatment apparatus in an embodiment according to the present invention.
Figure 4:
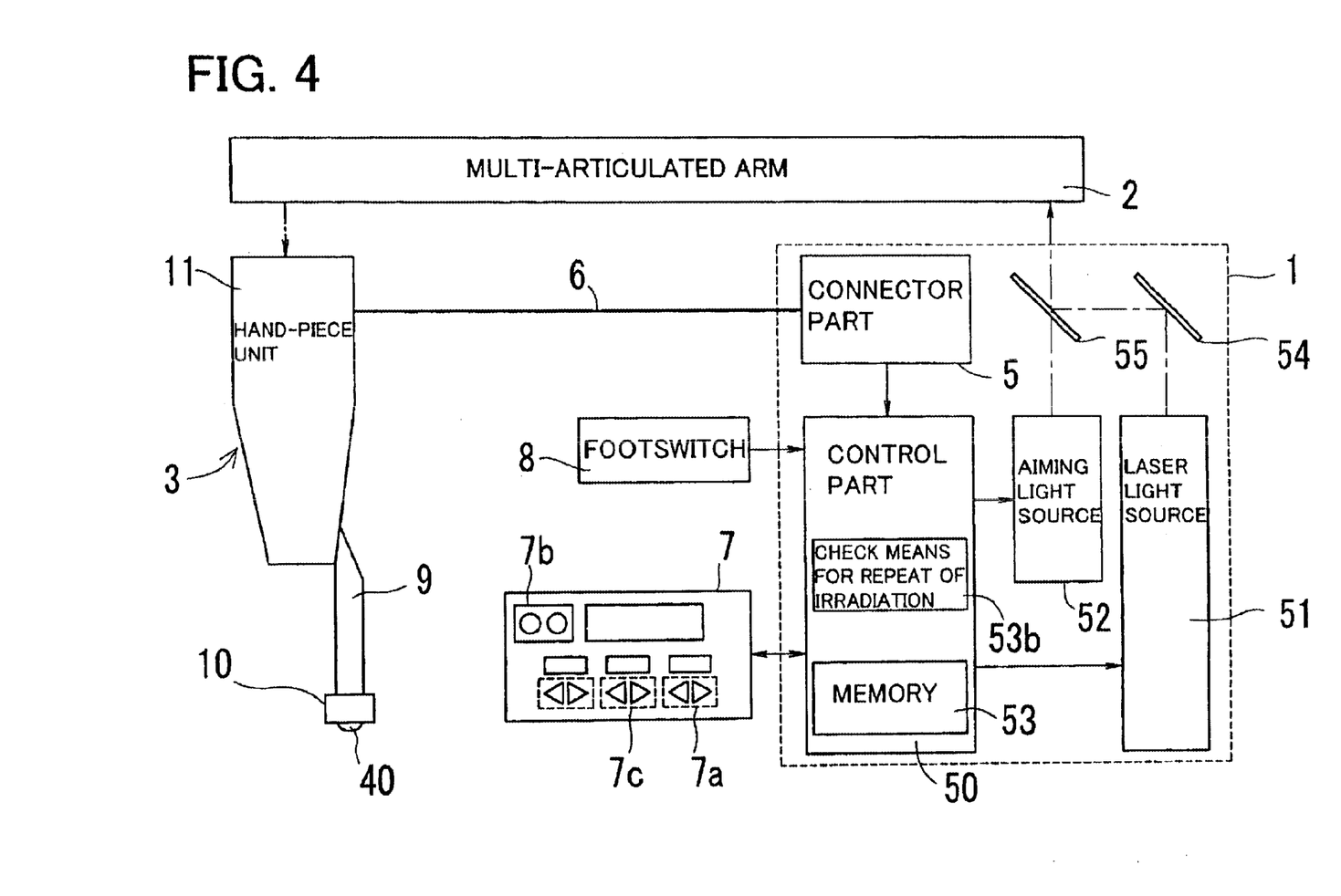
FIG. 4 is a schematic structural view of a main part of a control system and an optical system in the apparatus.

A detailed description of a preferred embodiment of a laser treatment apparatus embodying the present invention will now be given referring to the accompanying drawings, FIG. 1 is a schematic perspective view of the laser treatment apparatus in the present embodiment for performing treatment such as removal of wrinkles from the skin of a patient. FIG. 4 is a schematic structural view of a main part of a control system and an optical system in the apparatus.

Numeral 1 is a main unit of the laser treatment apparatus. This main unit 1 includes therein a light source 51 which emits a laser beam for treatment, a light source 52 which emits an aiming beam, an irradiation (light delivery) optical system, a control part 50, etc. In the apparatus in the present embodiment, the light source 51a is a $CO_2$ laser source which emits a pulsed laser beam of infrared light to be used as the treatment beam and the light source 52a is a laser diode which emits a red laser beam to be used as the aiming beam. Numeral 2 is a multi-articulated arm; 3, a hand-piece unit; 5 and 6, a connector part and a cable for receiving signals from the hand-piece unit 3; 7, a control panel for inputting various setting conditions including laser irradiation (irradiation of the treatment beam) conditions; and 8, a footswitch for generating a command signal for laser irradiation (a trigger signal).

The multi-articulated arm 2 is formed of several rigid pipes which are movably joined by joint portions, so that the operator can freely move the hand-piece unit 3 connected to the arm 2. In each joint portion of the arm 2, a mirror is disposed to deliver the treatment beam and the aiming beam discharged from the main unit 1 to the hand-piece unit 3 through the arm 2.

Figure 2:
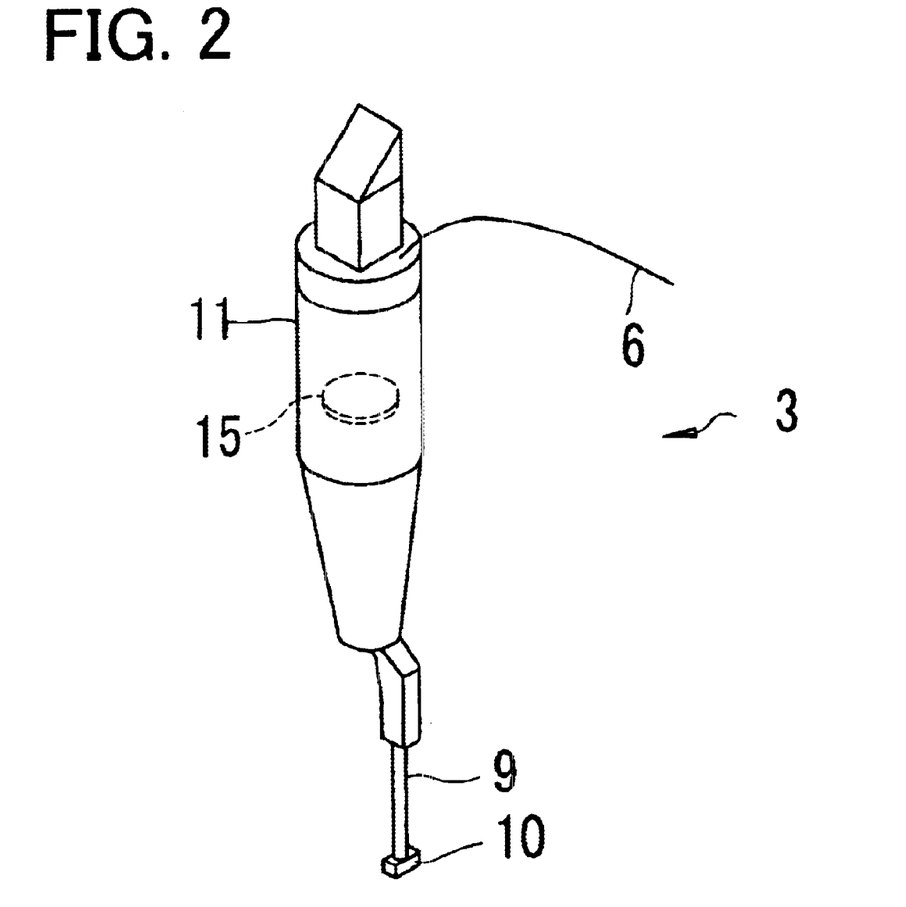
FIG. 2 is a schematic perspective view of a hand-piece unit in the embodiment.

FIG. 2 is a schematic perspective view of the hand-piece unit 3. This hand-piece unit 3 is constructed of a main body 11 internally provided with a light condensing lens 15 and a support rod (a distance keeping member) 9. This support rod 9 is provided, at its end, with a contact part 10 for contact with the skin of a patient. With the contact part 10 being in contact with the periphery (vicinity) of the treatment part (an affected part), the condensing lens 15 of the main body 11 can be held at a substantially constant distance from the treatment part. This makes it possible to place a focal point (an irradiation position, or a spot position) of the treatment beam which is condensed by the condensing lens 15 on the treatment part. The treatment beam is thus condensed into a predetermined spot size (diameter) on the treatment part. Since the contact part 10 is put on the periphery of the treatment part, wobbliness of the hand-piece unit 3 can be reduced. Accordingly, the laser irradiation can be performed in a state where the hand-piece unit 3 is held steady. The contact part 10 is provided with a mechanism for detecting the moved position of the hand-piece unit 3.

Figure 3A:
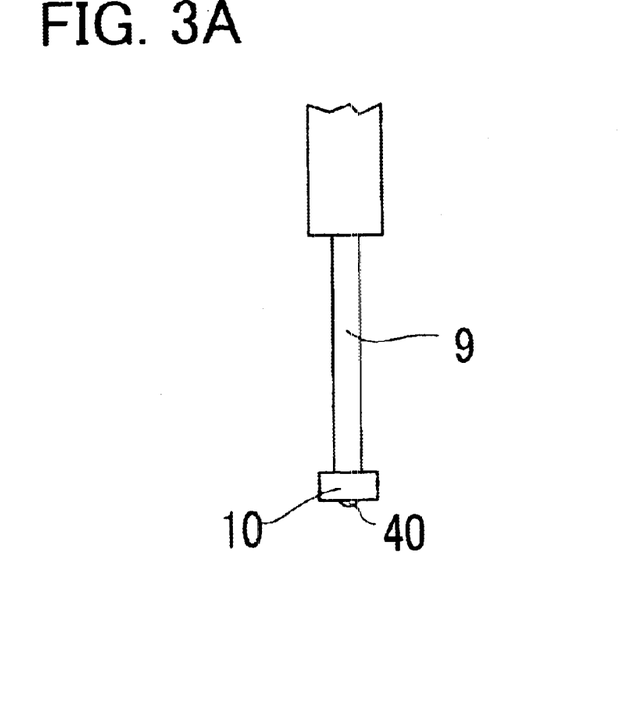
FIGS. 3A and 3B are schematic structural views of a moved-position detecting mechanism.
Figure 3B:
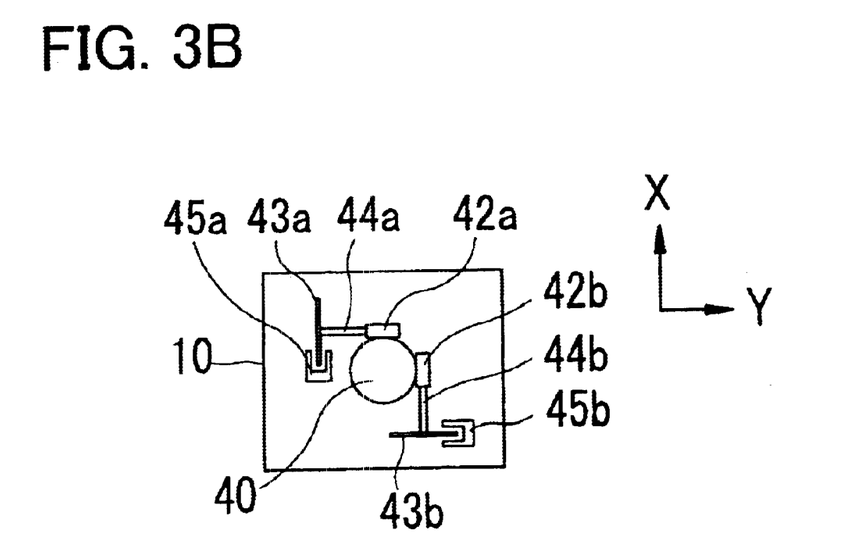

FIGS. 3A and 3B are explanatory views showing the moved-position detecting mechanism. FIG. 3A is a side view of the support rod 9 and the contact part 10. A ball 40 is provided in the contact part 10. To be more specific, the ball 40 is reliably disposed in the contact part 10 with only a part of the ball 40 projecting outside from the underside of the contact part 10.

FIG. 3B is a detailed view of an inside structure of the contact part 10. Rollers 42a and 42b are disposed rotatably in contact with the ball 40 and extending in directions perpendicular to each other. Rolling of the ball 40 causes the rollers 42a and 42b to rotate about shafts 44a and 44b respectively. Numerals 43a and 43b are rotating disks which are attached to the shafts 44a and 44b respectively. When the rollers 42a and 42b are rotated, accordingly, the rotating disks 43a and 43b are rotated in the same directions as the corresponding rotating directions of the rollers 42a and 42b.

The rotating disks 43a and 43b are each formed with slits arranged radially at circumferentially spaced intervals. Numerals 45a and 45b are photosensore each having a light projecting element and a light receiving element. These photosensors 45a and 45b are arranged so that each of the rotating disks 43a and 43b is positioned between the corresponding light projecting element and light receiving element. This mechanism is substantially the same as a mechanism for detecting a moved position of a mouse generally used in a personal computer or the like.

In the present embodiment, the detection of the moved position in a horizontal direction is based on the movement (the direction and amount of rolling) of the ball 40. The detection may also utilize a mechanism that allows a roller for an X-axis direction and a roller for a Y-axis direction to come in direct contact with the treatment part.

Furthermore, an optical means may also be used. For example, an illumination light is projected to the skin; a reflection light therefrom is received by a light receiving element; and the movement is detected based on an image obtained by the light receiving element.

Figure 6:
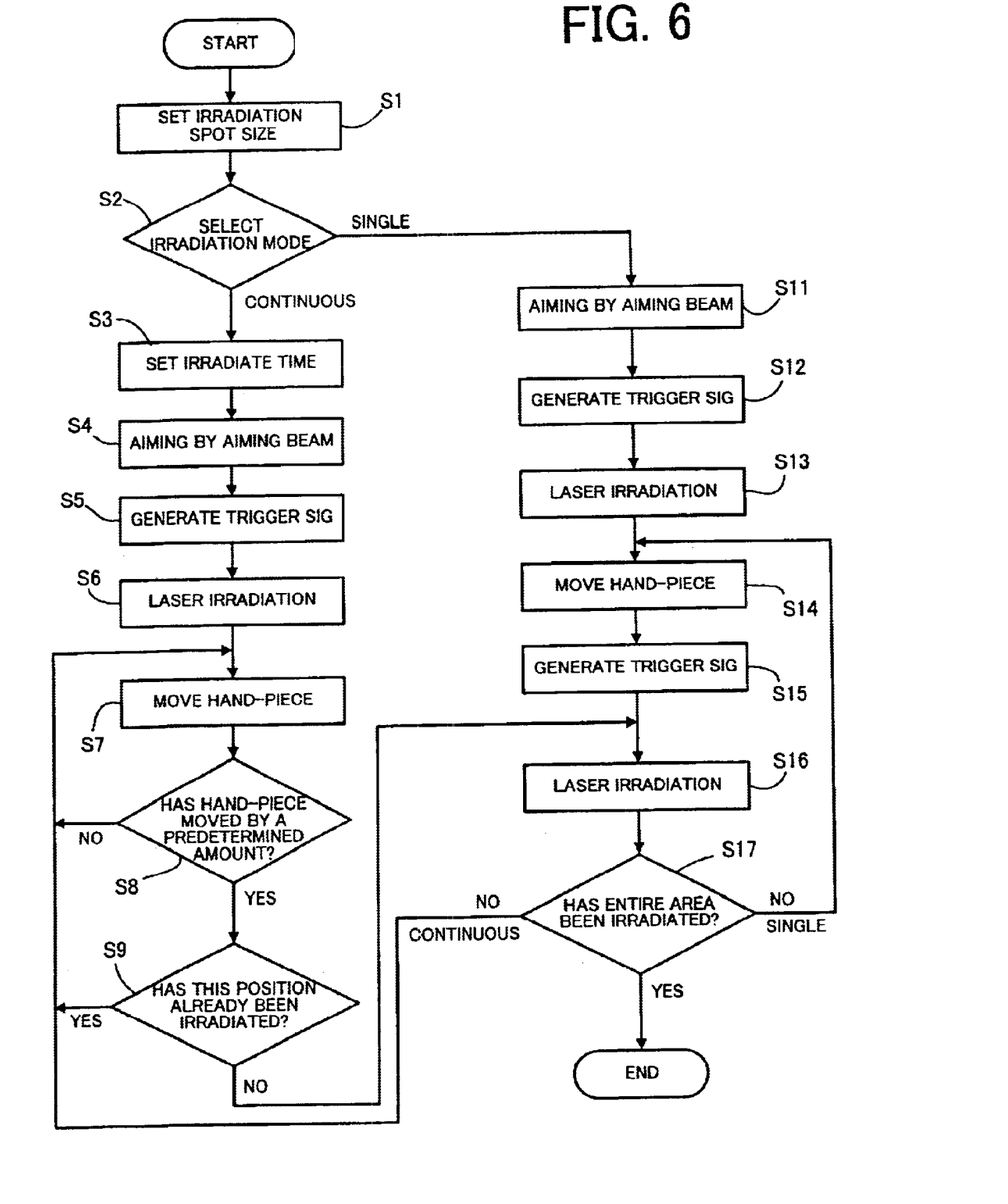
FIG. 6 is a flowchart showing a routine of operation of the apparatus in the embodiment.

The operation of the laser treatment apparatus having the above structure will be explained below with reference to FIG. 4 and FIG. 6.

The operator sets various laser irradiation conditions such as power and irradiation spot size of the treatment beam, irradiation intensity, and others by operation of switches on the control panel 7 (S1). If a hand-piece unit having a fixed spot size is used, the spot size may be set automatically in response to a signal representative of attachment of the hand-piece unit 3 to the arm 2. If another hand-piece unit having a variable spot size is used, on the other hand, the spot size may be set manually by operation of a switch 7a. The apparatus in the present embodiment is provided with a continuous irradiation mode (CONTINUOUS) and a single irradiation mode (SINGLE) as an operation mode. In the present embodiment, the continuous irradiation mode is selected by operation of a switch 7b (S2). When the continuous irradiation mode is selected (S2:CONTINUOUS), an irradiation time (3 msec) per pulse is set by the control part 50 (S3). It is to be noted that this irradiation time may be changed by operation of a switch 7c.

Upon completion of setting of the conditions, the operator holds the hand-piece unit 3 by hand and brings the contact part 10 into contact with the treatment part. At this time, an aiming beam is irradiated (discharged) from the hand-piece unit 3, and the operator recognizes an irradiation position of the aiming beam to aim at a first irradiation position while observing the aiming beam (S4). Upon completion of the aiming at the first irradiation position, the operator presses the footswitch 8 to generate a trigger signal (S5). Receiving the trigger signal, the control part 50 drivingly controls the light source 51 to emit a treatment beam (S6). The treatment beam emitted from the light source 51 is reflected by the mirror 54 and the dichroic mirror 55 in turn, then made coaxial with the aiming beam emitted from the light source 52, and becomes incident on the arm 2. The treatment beam (and the aiming beam) incident on the arm 2 is reflected by each mirror disposed in each joint portion and delivered into the hand-piece unit 3. The treatment beam (and the aiming beam) is then irradiated to the treatment part.

In the continuous irradiation mode, when the contact part 10 is moved in contact with the skin while the footswitch 8 is being pressed, the pulsed treatment beam is sequentially irradiated according to the moved position of the contact part 10. To be more specific, the operator moves the hand-piece unit 3 in contact with the skin in a direction that he intends to sequentially perform the laser irradiation (S7). The ball 40 in the contact part 10 rolls along the skin according to the direction and amount of movement of the hand-piece 3, causing the rollers 42a and 42b to rotate, thereby rotating the rotating disks 43a and 43b. The rotating states (the direction and amount of rotation) of the disks 43a and 43b are detected by the photosensors 45a and 45b respectively. The detection signals from the photosensors 45a and 45b are input to the control part 50. Based on the detection signals, the direction and amount of movement of the hand-piece unit 3 with respect to the treatment part are obtained and thus the moved position is detected.

When the hand-piece unit 3 has been moved by a predetermined amount (S8:YES), the control part 50 determines, based on the detection information on the moved position and the information on the irradiation spot Size, that the aiming at a nest irradiation point has been completed (S9:NO). At that timing, the control part 50 drivingly controls the light source 51 to emit the treatment beam. More specifically, when the hand-piece unit 3 is moved by a distance corresponding to the irradiation spot size while the footswitch 8 is being pressed (S8:YES), the treatment beam is emitted, thus irradiating the treatment part (S16). In this way, the operator does not have to recognize and adjust the aiming point every time the laser irradiation is performed. The laser irradiation can be executed efficiently with respect to a wide area. It is to be noted that the pulse time width of the treatment beam is usually short with respect to the speed of moving the hand-piece unit 3, and therefore the irradiation point will not be displaced so much. If the pulse time width of the treatment beam is set longer, the moving speed of the hand-piece unit 3 is requested only to be slowed.

The control part 50 stores each moved-position of the hand-piece unit 3 in a memory 53. The control part 50 can also control to prevent the position (area) that has been laser-irradiated once from being irradiated again. For this control, the control part 50 includes a programmed means 53b for checking and preventing a repeat of laser irradiation. This means 53b is concretely constructed of step 58 and S9 in FIG. 6.

Accordingly, it is possible for the operator to perform uniform laser-irradiation to the affected part with a simple operation as if he colors in a line-drawing with a colored pencil.

Figure 5:
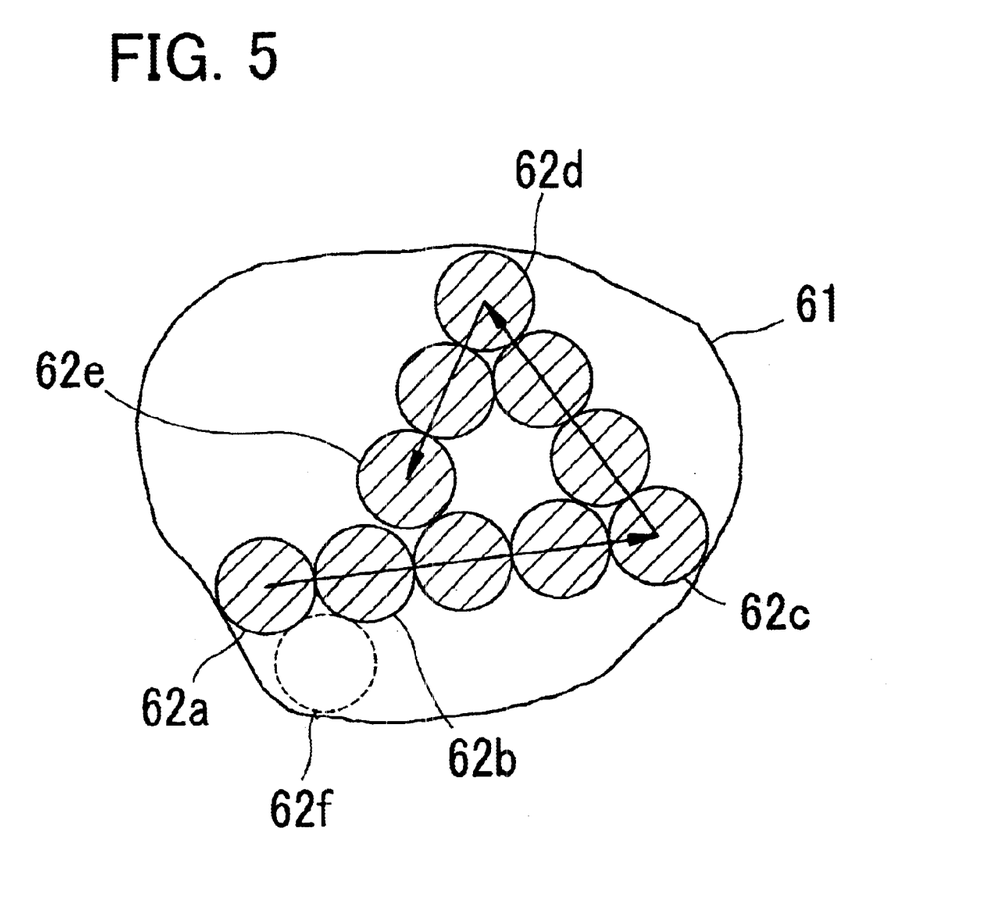
FIG. 5 is an explanatory view showing a laser irradiation method by movement of the hand-piece unit.

For instance, a case of irradiating a treatment area 61 shown in FIG. 5 is explained below. The laser irradiation is performed with respect to an irradiation spot 62a for a first time, and an irradiation spot 62b for a second time. In this case, the control part 50 determines an irradiation spot size (diameter) of the irradiation spot 62a as a one-pitch move amount. When the amount of movement determined based on the rolling of the ball 40 in the contact part 10 reaches the one-pitch move amount, the control part 50 controls to perform the laser irradiation (S8:YES and S9:NO). Similarly, the operator executes the laser irradiation toward an irradiation spot 62c, an irradiation spot 62d, and an irradiation spot 62e sequentially. According to the one-pitch move amount, a next spot to be irradiated after the spot 62e will be the spot 62b again. However, the control part 50, storing the positions where the hand-piece unit 3 has been moved before, controls to prevent a repeat of irradiation to the spot 62b which has been laser-irradiated once ($9:YES) and to turn the laser irradiation into an ON state when the irradiation position skips over the spot 62b and reaches the spot 62f. After the laser irradiation to the irradiation spot 62f, the operator moves the hand-piece unit 3 to continue the laser irradiation so that the entire treatment area 61 is fully irradiated. In the above way, the operator can easily perform the laser irradiation as if he colors in the treatment area 61 with a colored pen. As a result, the laser irradiation can be appropriately executed with respect to the entire area of the treatment part (S17).

If a narrow area or an unirradiated small portion is desired to be irradiated, the single irradiation mode should be selected (S2:SINGLE) to execute the laser irradiation to the targeted area or portion upon aiming thereat as in the conventional manner.

More specifically, the operator adjusts the aiming beam to the targeted (irradiation) position (S11) and presses the footswitch 8 to generate a trigger signal (S12) to perform laser irradiation (S13). Then, the operator moves the hand-piece unit 3 to another irradiation position (S14) and presses the footswitch 8 to generate a trigger signal (S15) to conduct laser irradiation (S16). The data on those irradiated positions are stored in the memory 53 in addition to the data on the entire area irradiation to check and prevent a repeat of irradiation to the entire area of the treatment part.

It is to be noted that an ON/OFF state of the laser irradiation may be controlled by insertion/removal of a shutter with respect to an optical path of the treatment beam, instead of direct control of the light source 51.

As with the mouse, the contact part 10 may be provided with a contact pressure detecting mechanism in addition to the movement (moved-position) detecting mechanism. In this case, the laser irradiation may be controlled to turn into an OFF state when a detected contact pressure is a predetermined value or less.

In order to prevent excessive tilt of the hand-piece unit 3 (the support rod 9 and the contact part 10) which may cause a problem that the ball 40 can not roll, a sound or the like may be produced to inform the operator that the hand-piece unit 3 is tilted beyond a predetermined permissible degree.

As explained above, according to the present invention, the laser irradiation can be efficiently and appropriately executed over a wide treatment area.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus for performing treatment on a treatment part of a skin by irradiating the part with a laser beam for treatment, the apparatus including:

laser output means which outputs the treatment beam;

a hand-piece provided with at least a part of an irradiation optical system for irradiating the treatment beam of a predetermined spot size, the hand-piece being held in contact with the skin;

detection means which detects a moved position of the hand-piece on the skin;

control means which controls an ON/OFF state of laser irradiation based on the moved position detected by the detection means and information on the spot size;

signal input means which inputs a command signal for the laser irradiation; and mode selection means which selects between a continuous irradiation mode where the ON/OFF state of the laser irradiation is controlled by the control means while the command signal is being input and a single irradiation mode where the laser irradiation is turned into the ON state every time the command signal is input.

2. The laser treatment apparatus according to claim 1, wherein the hand-piece includes a main part having at least the part of the irradiation optical system and a support part which is held in contact with the skin for supporting the main part above the skin, and the detection means includes a moved-position detector disposed in a side of the support part which comes into contact with the skin.

3. The laser treatment apparatus according to claim 2, wherein the moved-position detector is provided with a rolling member which is brought into contact with the skin and a rotation sensor for sensing a direction and amount of rotation of the rolling member, and the detection means obtains a direction and amount of movement of the hand-piece based on the rotation direction and the rotation amount detected by the rotation sensor, and detects the moved position of the hand-piece.

4. The laser treatment apparatus according to claim 1 further including storage means which stores the detected moved-position, wherein the control means controls the ON/OFF state of the laser irradiation based on the stored moved-position as well.

5. The laser treatment apparatus according to claim 1, wherein the laser output means includes a laser light source which emits a pulsed treatment beam.

6. A laser treatment apparatus for performing treatment on a treatment part of a skin by irradiating the part with a laser beam for treatment, the apparatus including:

a treatment laser beam output device;

a hand-piece provided with a main part having at least a part of an irradiation optical system for irradiating the treatment beam of a predetermined spot size and a support part which is held in contact with the skin for supporting the main part above the skin;

a rolling member provided in a side of the support part which is brought into contact with the skin;

a rotation sensor for sensing a direction and amount of rotation of the rolling member;

a controller which detects a direction and amount of movement of the hand-piece on the skin based on the rotation direction and the rotation amount detected by the rotation sensor, detects a moved position of the hand-piece based on the detected movement direction and the detected movement amount, and controls an ON/OFF state of laser irradiation based on the detected moved-position and information on the spot size;

a signal input unit which inputs a command signal for laser irradiation; and a mode selection unit which selects between a continuous irradiation mode where the ON/OFF state of the laser irradiation is controlled by the controller while the command signal is being input and a single irradiation mode where the laser irradiation is turned into the ON state every time the command signal is input.

7. The laser treatment apparatus according to claim 6 further including a memory for storing the detected moved-position, wherein the controller controls the ON/OFF state of the laser irradiation based on the stored moved-position.

* * * * *